United States Patent [19]

Heinl

[11] Patent Number: 4,903,691

[45] Date of Patent: Feb. 27, 1990

[54] SET OF SURGICAL INSTRUMENTS FOR JOINING BONE FRAGMENTS

[76] Inventor: Thomas Heinl, Rottendorfer Strasse 22a, D-8708 Gerbrunn, Fed. Rep. of Germany

[21] Appl. No.: 5,718

[22] Filed: Jan. 21, 1987

[30] Foreign Application Priority Data

Jan. 22, 1986 [DE] Fed. Rep. of Germany ....... 3601715

[51] Int. Cl.$^4$ .............................................. A61F 5/04
[52] U.S. Cl. ..................................................... 606/70
[58] Field of Search ........... 128/92 V, 92 YP, 92 YF; 81/451

[56] References Cited

U.S. PATENT DOCUMENTS

| | | | |
|---|---|---|---|
| Re. 28,841 | 6/1976 | Allgower et al. | 128/92 YP |
| Re. 31,628 | 7/1984 | Allgower et al. | 128/92 YP |
| 701,941 | 6/1902 | Rowlands | 81/451 |
| 768,441 | 8/1904 | Fisher | 81/451 |
| 772,912 | 10/1904 | Allam | 81/451 |
| 775,427 | 11/1904 | Lusted | 81/451 |
| 1,105,105 | 7/1914 | Sherman | 128/92 YP |
| 2,329,398 | 10/1943 | Duffy | 128/92 U |
| 2,765,828 | 10/1956 | Leniz | 81/451 |
| 2,780,257 | 2/1957 | Duggan | 81/451 |
| 2,792,861 | 9/1952 | Baker | 81/451 |
| 2,839,815 | 6/1958 | Reeves et al. | 128/92 YF |
| 3,236,275 | 2/1966 | Smith | 128/92 U |
| 3,680,553 | 8/1972 | Seppo | 128/92 YP |
| 3,779,240 | 12/1973 | Kondow | 128/92 YP |
| 4,029,091 | 6/1977 | von BeZold et al. | 128/92 YP |
| 4,119,092 | 10/1978 | Cril | 128/92 YP |
| 4,120,298 | 10/1978 | Fixel | 128/92 YP |
| 4,219,015 | 8/1980 | Steinemann | 128/92 YP |
| 4,263,904 | 3/1981 | Judet | 128/92 YP |
| 4,388,921 | 6/1983 | Sutter et al. | 128/92 YP |
| 4,429,690 | 2/1984 | Angelino-Pieuani | 128/92 YP |
| 4,484,570 | 11/1984 | Sutter et al. | 128/92 YP |
| 4,503,848 | 3/1985 | Caspar et al. | 128/92 YP |
| 4,541,422 | 9/1985 | de Zbikowski | 128/92 U |
| 4,612,921 | 9/1986 | de Zbikowski | 128/92 YF |
| 4,651,724 | 3/1987 | Berenley et al. | 128/92 YP |
| 4,683,878 | 8/1987 | Carter | 128/92 YP |
| 4,696,290 | 9/1987 | Steffee | 128/92 YP |

Primary Examiner—John D. Yasko
Attorney, Agent, or Firm—Edwin D. Schindler

[57] ABSTRACT

This invention concerns a set of surgical instruments for joining bone fragments (osteosynthesis) by screw fastening, especially in the case of cranial, facial, vertebral or hand fractures, comprising several plates of different shapes and curvatures and with holes and/or several screws and/or a screwdriver 8 and/or a bending instrument and/or a depth gauge and/or a drill and/or a cutting instrument. Special designs of said plates, screws and also said screwdriver 8 are given, whereby the latter comprises a blade 10, coaxially and movably a collet 11 with, at the lower end, radial, spring-supported jaws 15 and on said collet 11 an axially slidable retaining sleeve 12, which in its lowermost position presses said jaws 15 inwards.

37 Claims, 1 Drawing Sheet

SET OF SURGICAL INSTRUMENTS FOR JOINING BONE FRAGMENTS

This invention comprises a set of surgical instruments for joining bone fragments (osteosynthesis). More particularly, the present invention relates to a set of surgical instruments for joining bone fragments involving cranial, facial, vertebral, or hand fractures.

In surgery it is the general practice to join bone fractures, caused in accidents or by surgical operations, among other methods, by screwing or joining the fragments by means connecting plates. By comparison with other, in principle, conceivable methods, the screw technique is to be recommended, particularly when the separate bone fragments must be very firmly and precisely aligned with respect to each other, as is especially the case with cranial, facial, vertebral, or hand fractures. After the separate bone fragments have healed, the plates, if made of non-resorbable or less compatible material, are removed by a subsequent surgical operation. For implantation, flat plates with equidistant holes are available as being state of the art, which must be adapted to specific requirements by, at least partially, bending them, during the operation with a suitable set of instruments. Fastening is done with slot-head screws of normal construction, which are, for their part, inserted with screwdrivers such as are known per se from mechanical engineering. It needs no further explanation that a considerable extension to the operation time is produced by the separate plates having to be adapted and, for example, bend during the operation, and that great risk is involved in handling screw and screwdriver require that constant care must be taken that the screw on the screwdriver does not fall off immediately before being inserted into the bone, and be lost in the operation wound, which would lead to serious additional complications. It goes without saying that here, as with all other operations, the operation time itself must be kept as short as possible in order to reduce the stress to the patient.

Accordingly, it is an object of the present invention to provide an improved set of surgical instruments for use in joining bone fragments which permits the joining of such fragments in a more efficient, quicker and safer manner.

The foregoing and related objects are accomplished by the present invention, which includes a set of instruments having several plates of different shapes and curvatures and having holes and/or several screws and/or a screwdriver and/or a bending instrument and/or a depth gauge and/or a drill and/or a cutting instrument. In order for the work to be possible at all, the set of instruments must in its minimum configuration comprise plates, screws, and a screwdriver.

The other instruments listed, on the other hand, can considerably aid the work, they are, however, not absolutely necessary. The gist of the present invention resides in the making available of a set of instruments that provides the surgeon with all necessary tools and prosthetic elements.

One of the crucial concepts of the present invention is to replace the presently used flat plates, which are without exception of equal size, with an assortment of differently shaped and curved plates provided with multiple holes to subsequently receive screws. It is thus possible for the surgeon, taking into account the particular anatomical conditions and also the particular statical portions, especially with respect to loads and flexural moments occurring at that point, to select the plate best suited for its shape and form and use it immediately. The adapting or bending operation, which was previously generally necessary, is then largely made superfluous, so that much faster work is possible. Naturally, the dimensions and curvatures of the plates will be adapted to the respective application, so that different sets, i.e. plates of different shapes and sizes for adults and children, in cranial and hand surgery, etc. will be available. Furthermore, the curvature of the plates will be approximately adapted to subsequent conditions, i.e. in oral or facial surgery the shape of the plates will be adapted according to the anatomical profile of jawbone, face and cranium. Adaptation of the plates with the aid of the bending instrument to the respective curvatures is then largely eliminated.

As concrete embodiment of the individual plates, L, T, double-T, Y, double-Y, S, H-shapes are proposed, whereby in the case of the L and T-shapes, the angle enclosed by the two legs need not be exactly 90 degrees but can deviate from this, e.g. may also be 80 degrees. Furthermore, plates of arcuate form can be provided, which would be suitable for application in the vicinity of the infraorbital edge. Naturally, the curved elements can thereby etend in various directions and planes, so that in the end result, a three-dimensionally structured and aligned plate is obtained. An example of this is the so-called jawbone angle plate. By combination of different forms, a plurality of available shapes is produced, making available to the operating surgeon the suitable plate for implantation in every situation and position.

In an expedient embodiment, it is proposed so to extend the plates, concretely described above, to the effect that at their end points are located additional, preferably two-armed, but not excluding multi-armed, branches, which are arranged singly or multiply in series and in the most general case possess asymmetries even when the basic form is symmetrical. Thereby the ease of fastening the plates at their end points is improved because of the holes located there. This is insofar advantageous as the end points come to lie in the area of the bone fragments and thereby can be easily fastened, the central areas on the other hand cannot be fastened because of the gap which may very probably be found there. In the special case of the T-shape, a so-called nasal-piece can be created in this manner, with the help of which a particularly good bridging and linking of the frontal region with the nasal region can be achieved.

For introducing the holes, into the plates it is for the same reason of special advantage if they are disposed at the ends of the plates, since introduction of screws into the central area is generally not possible because the bone fracture is located there and the screws would be useless. Otherwise the arrangement of the holes is optional, and may be symmetrical or asymmetrical.

For fractures with a plurality of small bone fragments the invention recommends the use of a multi-fragment plate, which comprises a plurality of closely spaced holes. This is utilized whereby the plate is laid on the splintered fracture and, depending on the particular profile of the fracture, the screws are screwed into those openings beneath which a coherent bone fragment is located, so that the screws can grip readily. The sieve-like structure of a multi-fragment plate of this nature permits the simultaneous inclusion of a plurality of bone fragments.

In an expedient embodiment a screw ring, which surrounds the screw that is subsequently to be received has a higher strength than the other part of the plate. This result can be achieved in various ways, for example wherein the width of the plate in the area of the screw ring, even deducting the clear width, is large than a width of the web between the two rings. This thereby ensures that during bending, the screw ring remains largely undeformed and only the area between is appreciably bent and thereby lends the plate its desired form. Appreciable deformation of the screw ring itself results, disadvantageously, in a reduction of the clear cross-section of the same and thereby difficulties in introducing the screw or defective seating of the screw. If the deformation occurs principally in the vicinity of the web between the screw rings, these disadvantages do not occur.

In a preferred embodiment, the outer contour of the plate is to be completely or partially formed as an arc and, if necessary, as a straight profile. This has the advantage of a saving in surface area and thereby in material whilst retaining the stability. Additionally the nutrition of the bone located beneath is improved. Furthermore the negative effects of foreign matter are thereby reduced. In principle, certain areas of the exterior contours could thereby be chosen as straight lines in order, for example, to facilitate and improve the insertion of bending instruments at these points, for example, in the central region. In principle, the possibility also exists of forming the web on one side straight and the corresponding contour as a curve. The advantage of the straight line lies in aiding the precise assessment of the treated fracture on account of the reference line formed here. At the same time the advantages of the curved contour are retained, at least on one side.

It is furthermore proposed that the exterior contour of the plate be provided with toothing. This permits direct superimposition and interlocking of different plates, so that additional mutual stabilization of different plates is achieved. Furthermore there is the advantage that in the case of badly splintered fractures, inadequately secured bone fragments can be additionally secured by the additional connection between the plates. In effect, a maximum degree of stability of complicated bone fractures is obtained by highly the optional combination of individual plates in the manner of a modular system. By "toothing" in the sense of this invention is thereby to be understood as all kinds of deformation that permit mutual interlocking and connection. Corrugated contours, especially, are to be understood thereby.

It is of considerable advantage to design the plates as mirror-symmetrical pairs with respect to the shape and the arrangement of the holes. They are to be especially recommended because most bones are arranged in pairs, and therefore require two mirror-image plates for fractures. If the connection can be achieved with a single plate, the stability is increased. This applies equally even if the bones themselves are arranged mirror-symmetrically, as for example for nasal structures. Here, too, the stability is higher and the handling simpler than would be possible with two or more plates. A further advantage can be seen in the fact that a division of the plate along the axis of symmetry is possible, so that in the case of a fracture of bones with paired structure in only one half, the damaged side can be readily and easily tended alone. A further proposal is to round off all edges in order to remove the risk of perforating a soft covering on the plate and, furthermore, to promote and aid the build up and formation of the nuturing periosteum.

Graduation markings on the surface of the plate aid any necessary shaping of the plate, since they permit the shaped parts to be better defined and identified. Furthermore, the choice of the correctly sized plate is aided, and an orientation provided.

Finally, it is of considerable advantage to arrange the holes in the plates so that their centers lie on a curve whose profile is chosen such as to reproduce the averages of anatomical dimensions. The result is thereby achieved in many cases, namely when approximately average proportions are present, that the holes and screws fit exactly and can be screwed together. The curve defined by the holes describes the profile of a bone of average dimensions.

A further important concern of this invention is the improvement of the screws used to fasten the plates. In the state of the art, cross-head or slot-head screws with a pitch of about 1 mm are used. As an improvement, it is proposed to provide the slot-head screws with axial holes whose depth is larger than that of the slot and/or whose diameter is greater than or equal to the width of the slot. When a corresponding screwdriver is used, which is described in detail below, or whose blade is disposed an additional pin pointing in the axial direction, through the engagement of the blade in the slot and the pin in the axial hole are obtained a higher transversal stability, optimum force transmission and friction as well as better guidance in the axial direction, so that the work is considerably facilitated and furthermore the possibility of the screw falling off the blade is prevented. The same object is achieved if the diameter of the hole is greater than the width of the slot.

The screwing operation is made considerably easier if the tip of the screw is formed as a self-tapping bit. If a notch for chippings is additionally provided, the insertion torque for the self-tapping screw is reduced and the bone chips formed thereby collect in the notch and are retained. By providing an axial hole, the contact between the screw and screwdriver is improved so that the use of flat screw heads, by comparison with cross-head and Allen screws, is possible. When implanted, a smooth and flat surface is produced in combination with the plate. This has the advantage that contact points for friction are eliminated and the screw heads cannot penetrate the, often very thin, soft covering, so that the healing process is accelerated. By the term "flat screw head" is to be understood all screws for which the diameter of the head is at least double its height. In addition to a flat structure there is a further advantage in that the, often very thin, skin or mucous covering is not perforated.

Additionally, the circumference of the equator of the screw head should be greater than that of the cylinder below it and/or be formed as a cylinder sleeve. By the term equator is here understood the largest circumference of the screw head is a radial plane. With the dimensions of this invention, the screw head can be gripped from behind with the tool so that a better purchase and a larger contact area are provided.

At the same time a more sturdy screw head is obtained by the enlargement, which permits a higher load-bearing capacity and consequently also the exertion of a higher torque. Especially when using the screwdriver that is described in detail below, the complete screw head can be grasped during the first phase of introducing the screw, and during subsequent screwing in it, can be released and the rotary movement be transmitted only by the blade permitting a high penetration depth to be achieved, and consequently the use of shorter screws. This, too, requires a sturdy screw head, since with increasing penetration depth the forces to be imparted by the blade increase and must be transmitted. It must be constantly ensured that snapping of the screw is not possible and cannot occur under the ensuing higher loadings. The shape of the cylinder sleeve aids the provision of a large surface-area and therefore stable contact.

It is of special advantage that the screw be formed spherical below the equator and consequently also the hole in the plate. Even with excentric or inclined holes, there is then a circular, and therefore large area, contact of the screw in the corresponding hole in the plate. The seating of the screw and the connection to the plate are still optimally retained.

Through the measures of enlarging the central slot in the screw head and the blade of the screwdriver at one or two sides at the ends, safeguarding is obtained against transverse slipping within the slot.

It is especially advisable to dispose different screw pitches on one and the same shank. Then bone fragments can be pressed together in a similar way to a tension bolt, with the advantage that not only the screw head, but the thread together with the screw head, serves as an abutment. Furthermore, it is no longer necessary to drill a fragment.

As material for the plate and/or screw; and titanium and/or niobium and/or tantalum and/or gold and/or V2A and/or V4A grades of steel and/or ceramic and/or sapphire and/or carbon fibers and/or resorbable material such as polydioxanone, and/or other tissue-compatible are recommended. The advantage of titanium, as well as of niboium, gold and tantalum is the high tissue compatibility, even with long-term contact. Outstanding biocompatibility is combined with good strength and dimensional stability in these metals. In addition to the outstanding tissue compatibility, the high corrosion resistance of these metals is to be pointed out. Furthermore, no carcinogenic properties, allergic reactions, or growth inhibition are known. Because of these properties, these metals are excellently suited for implantation, and, with certain reservations, this applies to all the alloys made thereof, as well as to V2A and/or V4A steel. Independently of this, the use of resorbable material is provided for, which, by definition, dissolves after a certain duration in the body, so that, after regrowth of the bone fragments, the screws do not need to be unscrewed nor the plates removed, as is necessary in the state of the art. An example of a resorbable material is polydioxanone which dissolves by hydrolysis in the body after about 30 weeks. When such materials are used, a second operation to remove the plate is superfluous.

One of the main concerns of the present invention is the improvement and further development of the screwdriver belonging to the instrument set. The objective is to design the screwdriver so that it grips the screw securely and permits it to be screwed in precisely. Therefor it is proposed to dispose a collet coaxially on the blade of the screwdriver, with radially movable, spring-supported jaws at its lower end and an axially slidable retaining sleeve fastened spring-supported on the collet, which in its lower position presses said jaws inwards. Put simply, a screw retaining mechanism is to be disposed on the blade, which for its part includes a collet and a retaining sleeve. With the aid of the jaws in the collet, the head of the screw is gripped and by axial adjustment of the retaining sleeve toward the screw, held and screwed into the respective bone fragment. If the retaining sleeve is moved backwards, i.e., away from the screw, the jaws are released so that they move outwards by spring pressure and thereby release the screw head.

Irrespective of the position of the retaining sleeve and consequently of the jaws, the screwdriver is in contact with the screw via the blade, so that further turning of the screw is possible and a maximum insertion depth can thereby be achieved, since the screw head, which is normally gripped by the jaws, can be moved right into the plate or the bone fragment. The proposed construction thereby permits a greater insertion depth than would be possible with instruments that might enclose and hold the head during the complete insertion process. For better guidance, and to avoid losing the screw, in the solution of this invention the screw head is first grasped uniformly and circularly with the aid of the jaws in the collet, thereby providing it with a firm and secure purchase. When a certain penetration depth has been achieved, the screw head is released and the screw itself screwed in further only with the blade of the screwdriver, in order to reach a maximum penetration depth. Because of the spring construction of the jaws and especially the spring mounting of the retaining sleeve on the collet, it is additionally ensured that the retaining sleeve cannot readily fall forwards, e.g. under the effect of gravity, since a certain force needs to be exerted to overcome the spring forces, which, insofar as it is greater than the dead weight of the retaining sleeve, permits vertical work even with a retracted retaining sleeve. Additionally it must be mentioned that the collet is slidable on the blade against the force of the spring.

A further advantage can be seen in the fact that the grasping or release of the screw head acts as a circular movement, i.e. uniformly. Finally another decisive advantage can be seen in the facility of single-hand operation of the screwdriver of this invention. Both grasping and release of the screw head are performed by sliding the retaining sleeve, which can be done with one or two fingers of the hand holding the handle of the screwdriver. By the term "jaw" is meant that the screw head is enclosed at its outermost circumference, i.e. that the jaws have a circular internal grooved to receive the screw head.

Work can be especially simple and rapid if the collet can be slid only far enough over the blade for the jaws to enclose the screw head and the retaining sleeve cannot be slid beyond the end of the collet. The collet can then be moved forward as far as the stop and is then exactly positioned to grasp the screws. After the jaws have been pushed over the head, the are moved inwards onto the screw by movement of the retaining sleeve until contact. If the collet or retaining sleeve were movable further forwards, the collet would have to be precisely adjusted when grasping the screw head and retaining sleeve would cover the view of the screw thread during work.

In an expedient embodiment, a disk lying in a radial plane is molded onto the retaining sleeve with the help of which the adjustment, i.e. exact sliding, of the retaining sleeve is even simpler.

A further important concept of the present invention is in disposing a pin, that points in an axial direction on the blade of the screwdriver and using the slot-head screw already described above. The pin disposed on the blade of the screwdriver should then be dimensioned such that it engages in the axial hole so that compared with the handling a slot-head screw, an additional improvement of the guidance, particularly in the axial direction, and a high transverse stability can be achieved. Naturally, it is necessary to match or dimension the pin with respect to the axial hole in the screw.

It is of special advantage to choose the diameter of the pin greater than the thickness of the blade. Then a good transverse support and stability, i.e. acting in the direction of the slot, is achieved from the start when inserting the blade into the screw slot, and simultaneously the pin is protected. At the same time there is relatively intimate contact between blade and screw, if the blade is not yet at the base of the slot. With small pin diameters there would not be this advantage. Of course with corresponding dimensioning of the pin and blade, the screw-head must be complementarily formed.

In a preferred embodiment, the handle of the screwdriver is split and the two parts are movable radially and/or axially. It is then possible to hold the handle, and thereby the whole screwdriver with one part, and by rotation of the other, quickly and easily screw in or out a screw. Exact alignment whilst screwing the screw in or out is possible. Since the hand holding one part of the handle is held stationary and the rotational movement of the other part is carried out only by moving the fingers, the risk that the operation glove could be wound around the handle is eliminated. The axial adjustability permits the two parts to be moved with respect to each other by an axial pressing or pulling action, especially that they can engage and connect with each other. Particularly when loosening the screw it is important to achieve a high pressure with the blade and simultaneously to exert a high torque. This is made possible by the fact that the two parts can engage and consequently can be gripped by the whole hand and a considerably greater torque be exerted.

Further, it is part of this invention to accomodate a right/left ratchet mechanism and/or an adjustable torque limiter in the handle. The latter ensures that the maximum forces, which if exceeded would tear the head off the screw, cannot be exceeded. The right/left ratchet mechanism guarantees comfortable screwing in or out of the screw.

Finally, it is also part of this invention to support the blade in the handle on its face side. Then when large axial compressive loads are exerted, the consequential forces are transmitted not via the quick-release catch but directly to the blade, since otherwise premature wear with rapid loss of function would result.

To improve and aid the cleaning, disinfection, and sterilization of the screwdriver of this invention, blade, collet, retaining sleeve are separable and dismountable. The quick-release catch can be constructed in one of the ways known per se and to possess a hexagonal seat for the blade. An added advantage can be seen in the exchangeability of the separate elements in case of defects or different work lengths and blade diameters. Finally the seating of the blade, i.e., for example, the quick-release catch, is supported rotatably in the handle. This permits rotational movements of the blade to be carried out with a simultaneous spatially fixed handle. In practice, the rearmost fingers of the hand would hold the handle and the rotational movement necessary, to insert the screws, would be imparted by the front fingers by rotation of the blade seat, which must therefore be accessible from outside. The advantage is that the insertion can be carried out whilst retaining the axial position of the screw and with one hand. Fast and precise positioning of the screw in the respective bone fragment is the result. It is recommended that the seat of the blade be fixed by tension or pressure locked so that the full torque exertible by the whole hand can be transmitted.

The other individual devices forming part of the instrument set, such as the depth gauge, the drill, the bending and cutting instruments are not absolutely necessary for carrying out the work, but are advantageous and they are embodied in a manner known per se, so that any further explanation can be omitted here. By "bending instruments" what is meant here bending pliers, flat-nosed pliers, and also three-finger pliers. In a manner known per se, two pins are disposed on one leg of the pliers parallel to each other, onto which is laid the plate that is to be deformed or said pins are inserted into the holes, and, with another pin disposed approximately between the other two, said plate is deformed more or less severely when the pliers are operated. An existing striking surface guarantees that extreme and undesired deformations, even during rapid work, are not possible. This work, which is generally carried out during the operation, however, will generally become superfluous using the set of instruments of this invention, since, through the availability of plates of different shapes and curvatures, the most suitable plate can at any time be sought and immediately used. The cutting instrument serves to cut and adapt the plates.

Other details, features and advantages of the invention can be taken from the following detailed description in which, with the aid of the drawing, the embodiments of the set of surgical instruments of this invention are explained in greater detail.

The drawing figures shows schematically:

FIGS. 1–5 different representative shapes of the plates of this invention,

FIG. 6 a screwdriver of this invention in a dismounted condition.

FIG. 1 shows a plate of L-Form 1, whose longer legs has three holes 2 and whose shorter leg two holes (each including the hole at the corner point). Therefore for reasons of stability, the plate itself is enlarged in the area of hole 2 so that in case of deformations, the screw ring 3 surrounding hole 2 remains relatively unaffected, so that a screw can be inserted and passed through and an exact fit is achieved.

FIG. 2 shows a plate in the form of a double-Y, which also comprises holes 2 with surrounding screw rings 3. The only difference lies in the shape of the plate and in the number of holes 2 or screw rings 3.

In FIG. 3 a plate of approximately S-form 5 is shown, at whose outermost end three holes 2 with the accompanying screw rings are formed. In the center region in between lies the parting surface between the two bone fragments to be connected, so that the provision of holes in this area appears unnecessary.

FIG. 4 shows a multifragment plate 5 comprising a plurality of closely spaced holes, whereby a sieve-like structure occurs. The use of such a plate 5 is especially suitable for splinter fractures in which a plurality of closely space bone fragments have to be connected together. With the provision of a plurality of closely spaced holes 2 it is simple to introduce a screw into the optimum position in each bone fragment so that, in effect, several bone fragments can be connected with a single plate.

In FIG. 5, a nasal plate 6 is illustrated, which in its principal structure describes a "T", at whose end points two additional branches 7 are disposed. This nasal plate 6 is especially suitable for connecting the frontal plate with the nasal bone, whereby the longer axis is fastened to the frontal plate as an extension of the nasal bone and the two shorter axes vertically to this and legs lying in one axis bent around and fastened to the nasal bone at the sides. Fastening is primarily by means of two-armed branches disposed at the end points 7. The asymmetrical arrangement of branch 7 with reference to the two legs is done independently of each other for reasons of stability and improvement of the fastening of both legs.

FIG. 6 shows a screwdriver 8 of this invention in dismounted view for better clarification. This consists in its basic structure of a handle 9, a blade 10, a collet 11 and a retaining sleeve 12. The blade 10 is of conventional construction, consisting of a solid cylindrical rod and a tip 13. Departing from this, a pin 14, pointing in an axial direction, is additionally disposed approximately in the center, which engages in a corresponding axial hole of the screw to be fastened, which is not illustrated. Onto this blade 10 is pushed an essentially hollow-cylindrically shaped collet 11, which at its lower end is fitted with radially movable and spring-supported jaws 15. In the area of the jaws 15 the collet 11 has a slightly greater diameter. If the retaining sleeve, which is a hollow cylinder, is fitted, it must be pushed on from the top end and because of the internal diameter of said retaining sleeve 12 cannot be pushed beyond said jaws 15.

The handle 9 is of conventional construction and at its front end is equipped with a rotatable seat 16 for said blade 10. Assembly is done in the manner that, first said collet 11 is pushed onto said blade 10 and said retaining sleeve 12 is pushed thereon and the assembly thus formed is connected with the handle by inserting said blade 10 into said seat 16. The rotatability of the seat 16 guarantees that a rotary movement of said blade 10 can be made whilst said handle 9 is held stationary.

The invention is used in the manner that, with retract collet 11 and retaining sleeve 12, said blade 10, with its tip 13 and said pin 14, is inserted into the head of a corresponding screw with retracted retaining sleeve 12, and thereby with open jaws, said collet 11 is slid forwards until the screw head, which is not illustrated here, is enclosed. Then, for example with the aid of said disk 17, said retaining sleeve 12 is pushed forwards and thereby said jaws 15 moved inwards and said screw head gripped. Non-positive connections are thereby formed between said screw head and the inner face of said jaws 15, as well as the outer face of the latter and the retaining sleeve 12. The screw thread projects outwards and remains clearly visible. Now the lower end of the screw can be introduced into a corresponding hole 2 in a plate and, with axial pressure on said handle 9, be screwed in by rotary movement of said seat 16 until said jaws are almost in contact with the plate.

When said retaining sleeve 12 is retracted, said jaws move outwards again, releasing said screw head so that further screwing in of said screw to the final depth is done only with said blade 10 and via said pin 14. Both said retaining sleeve 12 and collet 11 are thereby spring supported so that in the retracted position, i.e. with open jaws 15, they cannot move of their own accord, so that work is possible even with said blade 10 in a vertical position and falling forwards of collet 11 and retaining sleeve 12 is prevented.

In summary, by this invention a set of surgical instruments is provided with the aid of which must faster and, at the same time, more precise work in the screw-fastening of bone fragments (osteosynthesis) is possible.

What is claimed is:

1. An assembly for joining bone fragments by osteosynthesis for cranial, facial, vertebral nor hand fractures, comprising:

a plurality of plates of various shapes and curvatures, each plate of said plurality of plates having one or more holes therein;

a plurality of screws for joining two or more bone fragments to one another with plates of said plurality of plates with each screw of said plurality of screws having a head with an equator which is formed as a cylindrical sleeve, said plurality of screws to communicate with the holes of said plurality of plates; and screwdriver means, having a blade and a handle, for joining bone fragments to one another with said plurality of plates by means of said plurality of screws.

2. The assembly according to claim 1, wherein at least one plate of said plurality of plates is L-shape.

3. The assembly according to claim 1, wherein at least one plate of said plurality of plates is T-shape.

4. The assembly according to claim 1, wherein at least one plate of said plurality of plates is double-T-shape.

5. The assembly according to claim 1, wherein at least one plate of said plurality of plates is Y-shape.

6. The assembly according to claim 1, wherein at least one plate of said plurality of plates is double-Y-shape.

7. The assembly according to claim 1, wherein at least one plate of said plurality of plates is S-shape.

8. The assembly according to claim 1, wherein at least one plate of said plurality of plates is H-shape.

9. The assembly according to claim 1, wherein at least one plate of said plurality of plates is an arcuate shape.

10. The assembly according to claim 1, wherein at least one plate of said plurality of plates includes a combination of two or more of the shapes of L-shape, T-shape, double-T shape, Y-shape, double-Y-shape, S-shape, H-shape and an arcuate shape.

11. The assembly according to claim 1, wherein at least one plate of said plurality of plates includes at least one end which is singly-branched.

12. The assembly according to claim 1, wherein at least one plate of said plurality of plates includes at least one end which is multiply-branched.

13. The assembly according to claim 1, wherein at least one plate of said plurality of plates includes a screw ring which surrounds a screw of said plurality of screws, said screw ring having a greater strength or rigidity than other portions of said plates of said plurality of plates.

14. The assembly according to claim 1, wherein at least one plate of said plurality of plates is contoured, with an exterior contour and an interior contour, said exterior contour being toothed.

15. The assembly according to claim 1, wherein at least one plate of said plurality of plates has an edge which is rounded.

16. The assembly according to claim 1, wherein at least one plate of said plurality of plates has graduation markings.

17. The assembly according to claim 1, wherein at least one screw of said plurality of screws is a slot-head screw having an axial hole, the depth of which hole being greater than or equal to the depth of the slot.

18. The assembly to claim 1, wherein at least one screw of said plurality of screws is a slot-head screw having a diameter which is greater than the width of the slot.

19. The assembly according to claim 1, wherein said plurality of plates is made of a tissue-compatible material.

20. The assembly according to claim 19, wherein said plurality of plates is made of a member selected from the group consisting of titanium, niobium, tantalum, gold, V2A-grade of steel, V4A-grade of steel, an alloy of V2A-grade of steel, an alloy of V4A-grade of steel, a ceramic material, sapphire, carbon fibers and a combination thereof.

21. The assembly according to claim 19, wherein said plurality of plates is made of a resorbable material.

22. The assembly according to claim 21, wherein said resorbable material is polydioxanone.

23. The assembly according to claim 1, further comprising a pin pointing in an axial direction, said pin being centrally-formed on said blade of said screwdriver means.

24. The assembly according to claim 1, further comprising a collet, having at a lower end, radially-movable, spring-supported jaws, said collet being disposed coaxially and slidably against the force of a spring or magnet on said blade of said screwdriver means, and an axially slidable retaining sleeve, being disposed and spring-supported on said collet, which, in a lower-most position, presses said clamping jaws inwardly.

25. The assembly according to claim 24, wherein said collet is maximally-slidable over said blade so that said clamping jaws are capable of gripping a screw head, said retaining sleeve being unslidable beyond said collet.

26. The assembly according to claim 24, wherein a handle of said screwdriver means is formed as having two parts, the two parts being movable with respect to one another radially.

27. The assembly according to claim 24, wherein a handle of said screwdriver means is formed as having two parts, the two parts being movable with respect to one another axially.

28. The assembly according to claim 27, wherein the two parts interlock under axial pressure.

29. The assembly according to claim 24, wherein a right/left ratchet mechanism is accommodated in a handle of said screwdriver means.

30. The assembly according to claim 24, wherein an adjustable torque limiter is accommodated in a handle of said screwdriver means.

31. The assembly according to claim 1, wherein the head of at least one screw of said plurality of screws includes a self-tapping bit.

32. The assembly according to claim 1, wherein the blade of said screwdriver means is recessed at its end.

33. The assembly according to claim 1, wherein the blade of said screwdriver means is extended at its end.

34. The assembly according to claim 1, wherein said plurality of screws have a central slot which is recessed at, at least, one end.

35. The assembly according to claim 1, wherein said plurality of screws have a central slot which is extended at, at least, one end.

36. The assembly according to claim 1, wherein said plurality of screws having different screw pitches which are applied to a single screw shank.

37. The assembly according to claim 14, wherein the teeth of said exterior contour are positioned in a plane which is defined by said plurality of plates.

* * * * *

(12) REEXAMINATION CERTIFICATE (4561st)
United States Patent
Heinl

(10) Number: US 4,903,691 C1
(45) Certificate Issued: Apr. 30, 2002

(54) SET OF SURGICAL INSTRUMENTS FOR JOINING BONE FRAGMENTS

(75) Inventor: Thomas Heinl, Rottendorfer Strasse 22a, D-8708 Gerbrunn (DE)

(73) Assignee: Thomas Heinl, Gerbrunn (DE)

Reexamination Request:
No. 90/005,275, Feb. 25, 1999
No. 90/005,809, Sep. 5, 2000

Reexamination Certificate for:
Patent No.: 4,903,691
Issued: Feb. 27, 1990
Appl. No.: 07/005,718
Filed: Jan. 21, 1987

(30) Foreign Application Priority Data

Jan. 22, 1986 (DE) .............................................. 3601715

(51) Int. Cl.⁷ .............................................. A61B 17/58
(52) U.S. Cl. ....................................................... 606/70
(58) Field of Search ............................. 606/70–72, 60, 606/65, 53, 104

(56) References Cited

U.S. PATENT DOCUMENTS

| | | |
|---|---|---|
| 2,288,584 A | 6/1942 | Longfellow |
| 2,370,407 A | 2/1945 | McCartney |
| 2,518,155 A | 8/1950 | Longfellow |
| 2,839,815 A | 6/1958 | Reeves et al. |
| 3,236,275 A | 2/1966 | Smith |
| 3,695,321 A | 10/1972 | Garehine, Jr. |
| 4,029,091 A | 6/1977 | von Bezold et al. |
| 4,190,091 A | 2/1980 | Colognori |
| 4,263,904 A | 4/1981 | Judet |
| 4,388,921 A | 6/1983 | Sutter et al. |
| 4,484,570 A | 11/1984 | Sutter et al. |
| 4,573,458 A | 3/1986 | Lower |
| 5,013,315 A | * 5/1991 | Barrows ...................... 606/71 |

FOREIGN PATENT DOCUMENTS

| | | |
|---|---|---|
| DE | GM 73 34 732 | 5/1975 |
| DE | 33 29 287 C2 | 2/1984 |
| DE | 35 39 502 C1 | 1/1986 |
| DE | G 85 28 004.6 | 1/1986 |
| EP | 0 048 038 | 3/1982 |

OTHER PUBLICATIONS

Medicon Instrumente Catalog, Original Steinhäuser, Jun. 1983, Cover Page, pp. 8, 9.

(List continued on next page.)

*Primary Examiner*—Michael J. Hayes

(57) ABSTRACT

This invention concerns a set of surgical instruments for joining bone fragments (osteosynthesis) by screw fastening, especially in the case of cranial, facial, vertebral or hand fractures, comprising several plates of different shapes and curvatures and with holes and/or several screws and/or a screwdriver 8 and/or a bending instrument and/or a depth gauge and/or a drill and/or a cutting instrument. Special designs of said plates, screws and also said screwdriver 8 are given, whereby the latter comprises a blade 10, coaxially and movably a collet 11 with, at the lower end, radial, spring-supported jaws 15 and on said collet 11 an axially slidable retaining sleeve 12, which in its lowermost position presses said jaws 15 inwards.

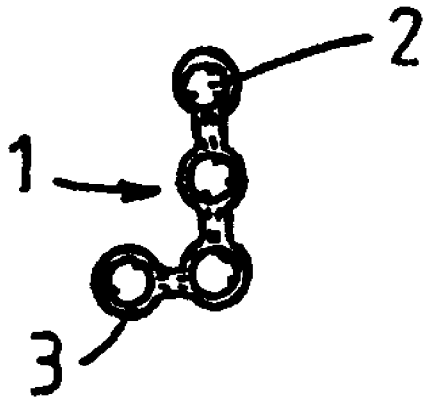

OTHER PUBLICATIONS

Figure 1:
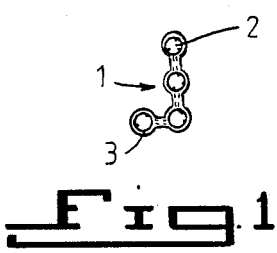
Figure 2:
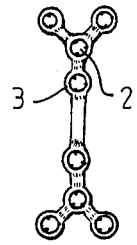
Figure 3:
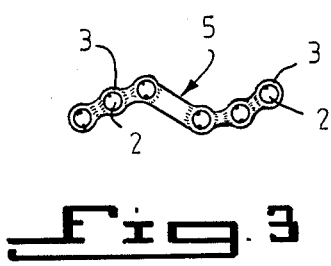
Figure 4:
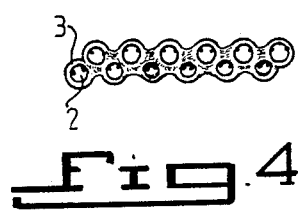
Figure 5:
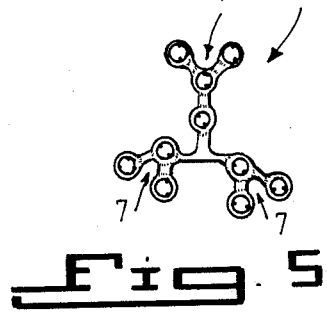
Figure 6:
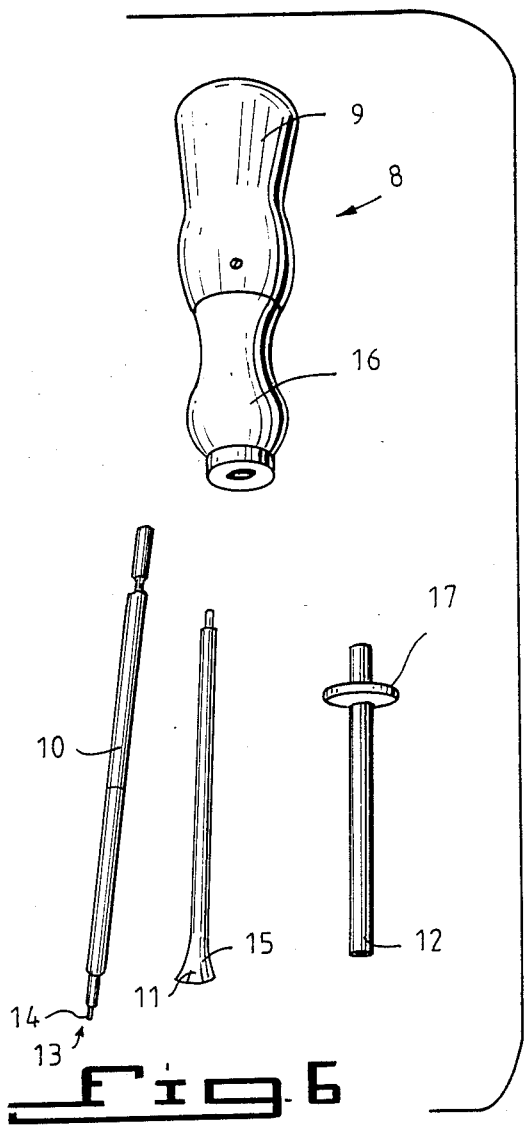

Howmedica Catalog, Mini–Compression System, 1985, Cover Page, pp. 22, 23, and other pages.
Martin Catalog, Maxillo–Facial Osteosynthesis by Small Plates, Feb. 1985, Cover Page, pp. 1–3.
Kloman Instrument, 1954 Edition Catalog, 1954, pp. F108, F111, F112, F114.
Oswald Leibinger, Titanium Mini–Plate System for Cranio–Facial Osteosynthesis, 1985, Cover Page and Subsequent Pages.
Aesculap Catalog, Ninth Edition, Mi–1950's, p. 167.
Medicon Instrumente Catalog, Bone Plates and Bone Screws, 1960, pp. 505, 507, 509.
MLW Catalog, Dec. 1975, pp. 14–16.
Martin Catalog, 1978, pp. 314, 315, 319.
Zimmer USA Catalog, Jun. 1978, pp. B20, B22, B26.
Aesculap Catalog 186–C, Aug. 1982, pp. N–1, 7, 29, 35, 36, also referred to as "1982 Catalog of Aesculap".
Downs Catalog, Mandibular Compression Plating System, 1984.
"Synthes" Rob. Mathys Catalog, 1983, p. 86.
German Standards DIN 58 812, 58 814, and 58 815, Published Mar. 24, 1982.
Publication Spezielle Frakturen–und Luxationslehre, Published in 1972.

* cited by examiner

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–37 is confirmed.

* * * * *